(12) United States Patent
Royalty

(10) Patent No.: US 8,231,517 B2
(45) Date of Patent: Jul. 31, 2012

(54) STABILIZATION FOR ELECTROMAGNETIC BIVENTRICULAR ASSIST DEVICE

(76) Inventor: John W Royalty, Crystal River, FL (US)

(*) Notice: Subject to any disclaimer, the term of this patent is extended or adjusted under 35 U.S.C. 154(b) by 784 days.

(21) Appl. No.: 11/648,635

(22) Filed: Jan. 3, 2007

(65) Prior Publication Data

US 2007/0156007 A1 Jul. 5, 2007

Related U.S. Application Data

(60) Provisional application No. 60/755,413, filed on Dec. 31, 2005, provisional application No. 60/755,414, filed on Dec. 31, 2005, provisional application No. 60/755,415, filed on Dec. 31, 2005, provisional application No. 60/755,416, filed on Dec. 31, 2005, provisional application No. 60/755,424, filed on Dec. 31, 2005.

(51) Int. Cl.
*A61N 1/362* (2006.01)
*A61N 1/00* (2006.01)

(52) U.S. Cl. .......................................... 600/16; 607/129

(58) Field of Classification Search .................. 607/129; 600/16
See application file for complete search history.

(56) References Cited

U.S. PATENT DOCUMENTS

| 5,182,533 | A | | 1/1993 | Ritts | |
|---|---|---|---|---|---|
| 5,498,228 | A | * | 3/1996 | Royalty et al. | 600/16 |
| 6,887,192 | B1 | * | 5/2005 | Whayne et al. | 600/16 |
| 2004/0162463 | A1 | * | 8/2004 | Lau et al. | 600/37 |
| 2005/0160823 | A1 | * | 7/2005 | Zdeblick et al. | 73/715 |

* cited by examiner

*Primary Examiner* — Nicole F Lavert
(74) *Attorney, Agent, or Firm* — Pillsbury Winthrop Shaw Pittman LLP

(57) ABSTRACT

An electromagnetic cardiac assembly adapted to assist ventricular output in a human heart includes a magnetic mat adapted for mounting inside a human body adjacent the heart. The mat is made from a material responsive to application of an electromagnetic field so as to be movable into compressive relation with the heart in response to application of the electromagnetic field thereto and movable out of said compressive relation to permit the heart to relax when application of said electromagnetic field is discontinued. The mat has a posterior surface that substantially conforms to an anterior surface of the heart without flexing the mat. The assembly also includes an electromagnetic subassembly adapted for mounting on the human body in functionally cooperative relation with respect to the mat, and for alternately generating and discontinuing the electromagnetic field so that the mat alternately moves into and out of the compressive relation with the heart.

20 Claims, 4 Drawing Sheets

STABILIZATION FOR ELECTROMAGNETIC BIVENTRICULAR ASSIST DEVICE

CROSS-REFERENCE TO RELATED APPLICATIONS

This application claims the benefit of priority from U.S. Provisional Patent Application Ser. Nos. 60/755,413, 60/755,414, 60/755,415, 60/755,416, and 60/755,424, all of which were filed Dec. 31, 2005, the contents of which are incorporated herein by reference in their entireties. The present application is related to U.S. patent application Ser. Nos. 11/648,914 (published as U.S. Patent Application Publication No. 2007-0238914 A1), 11/648,636 (published as U.S. Patent Application Publication No. 2007-0156008 A1), 11/648,637 (published as U.S. Patent Application Publication No. 2007-0156055 A1), and 11/648,908 (published as U.S. Patent Application Publication No. 2007-0250162 A1), all of which are being were filed on Jan. 3, 2007 and are currently pending, and the contents of all of which are incorporated herein by reference in their entireties.

BACKGROUND OF THE INVENTION

1. Field of Invention

This invention relates to cardiac assist devices, and more particularly, to a device and method for assisting ventricular output in the human heart.

2. Description of Related Art

During the aging process, weakened or ineffective cardiac muscles may inhibit the cardiac pumping function from either the right, left, or both ventricles. When the pumping activity of the heart cannot meet the body's demands, systemic shock and subsequent organ dysfunction (such as pulmonary edema and renal failure) can result. Weakened heart muscles can also result in an over distended, dilated myocardium, which can have a detrimental effect on the electrical conduction and overall mechanical performance of the heart.

Advances in medical science have attempted to overcome these problems by replacing an impaired heart via heart transplants, or with devices such as artificial hearts. However, heart transplants are difficult to obtain since there is a limited donor supply. Moreover, artificial hearts have proved not entirely effective in duplicating cardiac contractions, are extremely expensive, and are known to be rejected by the human body.

Therefore, rather than replacing the heart, various arrangements have been proposed to assist right and left ventricular output of the existing impaired heart. For example, a number of arrangements are suggested in U.S. Pat. No. 4,621,617 to Sharma ("the '617 patent"). FIG. 1 of the '617 patent proposes an arrangement in which two components are disposed in surrounding relation to the heart and function to compress the heart therebetween to assist ventricular output thereof. The two components are furnished with electromagnetic induction circuitry, numerous pole elements, and are secured to one another by a mechanical hinge. It can be appreciated that the device is quite cumbersome, difficult to implant, and has achieved little if any acceptance. FIG. 4 of the '617 patent illustrates an alternate arrangement in which a compressor element is provided posteriorly to the heart and is movable to compress the heart against the rib cage. This embodiment is somewhat more practical, but nevertheless problematic in a number of respects. For example, no means are provided for evaluating the amount of compressive resistance or intracardiac pressure of the heart during compression thereof. As a result, the compressor element may either apply insufficient compressive force to the heart, thereby resulting in ineffective ventricular assist, or apply excessive compressive force, thereby damaging the heart. Additionally, providing a compressor element posteriorly to the heart requires complex surgery in which the entire chest cavity must be opened. Moreover, such placement of the compressor element is largely impractical since the aorta, esophagus and spine are all disposed in close proximity to the posterior portion of the heart and leave little room for insertion of any type of assist device.

U.S. Pat. No. 5,498,228 ("the '228 patent"), which is incorporated herein by reference in its entirety, discloses an electromagnetic biventricular assist device that includes an inductive coil placed on the anterior surface of the chest of a human patient. When the coil receives current, a magnetic field is generated, which repels a magnetic mat that is located on the anterior surface of the heart posteriorly, thereby compressing the heart. These compressions are timed by a cardiogram so as to augment the systolic function of the heart. The morphologies of the electromagnetic field generated by the coil and the magnetic field generated by the magnetic mat are somewhat round. Although the coil is stabilized externally on the anterior surface of the chest, the magnetic mat has the freedom to flip, which would permit opposite poles created by the mat and the coil to attract. However, proper operation of the electromagnetic biventricular assist device of the '228 patent is dependent on like pole interfacing with like pole, so that a force may be exerted on the anterior surface of the heart via the mat, and energy may be transferred to the heart. Therefore, the more consistently a pole generated by the coil can interface with a like pole generated by the mat, the more consistently the device will function properly at the electromagnetic interface.

BRIEF SUMMARY OF THE INVENTION

It is desirable to improve the stabilization of the electromagnetic biventricular assist device described by the '228 patent.

In an embodiment of the present invention, an electromagnetic cardiac assembly that is adapted to assist ventricular output in a human heart is provided. The cardiac assembly includes a magnetic mat adapted for mounting inside a human body adjacent the heart. The mat is made from a material responsive to application of an electromagnetic field so as to be movable in a first direction into compressive relation with the heart in response to application of the electromagnetic field thereto and movable in a second direction out of said compressive relation to permit the heart to relax when application of the electromagnetic field is discontinued. The mat has a posterior surface that substantially conforms to an anterior surface of the heart without flexing the mat. The cardiac assembly also includes an electromagnetic subassembly adapted for mounting on the human body in functionally cooperative relation with respect to the mat, and for alternately generating and discontinuing the electromagnetic field so that the mat alternately moves into and out of the compressive relation with the heart.

In an embodiment of the present invention, an electromagnetic cardiac assembly that is adapted to assist ventricular output in a human heart is provided. The cardiac assembly includes a magnetic mat adapted for mounting inside a human body adjacent the heart. The mat is made from a material responsive to application of an electromagnetic field so as to be movable in a first direction into compressive relation with the heart in response to application of the electromagnetic field thereto and movable in a second direction out of the compressive relation to permit the heart to relax when application of the electromagnetic field is discontinued. The mat has a non-uniform thickness. The cardiac assembly also includes an electromagnetic subassembly adapted for mounting on the human body in functionally cooperative relation with respect to the mat, and for alternately generating and discontinuing said electromagnetic field so that the mat alternately moves into and out of the compressive relation with the heart.

In an embodiment of the present invention, an electromagnetic cardiac assembly that is adapted to assist ventricular output in a human heart is provided. The cardiac assembly includes a magnetic mat adapted for mounting inside a human body adjacent the heart. The mat is made from a material responsive to application of an electromagnetic field so as to be movable in a first direction into compressive relation with the heart in response to application of the electromagnetic field thereto and movable in a second direction out of the compressive relation to permit the heart to relax when application of the electromagnetic field is discontinued. The mat is constructed and arranged to generate a plurality of magnetic fields. The cardiac assembly also includes an electromagnetic subassembly adapted for mounting on the human body in functionally cooperative relation with respect to the mat, and for alternately generating and discontinuing the electromagnetic field so that the mat alternately moves into and out of the compressive relation with the heart. The electromagnetic assembly includes a plurality of coils constructed and arranged to generate a plurality of electromagnetic subfields that together form the electromagnetic field. The electromagnetic subfields are arranged to extend in between the plurality of magnetic fields created by the mat when the mat and the electromagnetic subassembly are mounted to the human body so as to create a locking relation between the electromagnetic subassembly and the mat.

In an embodiment of the present invention, a method for stabilizing an electromagnetic cardiac assembly is provided. The assembly includes a magnetic mat adapted for mounting inside a human body adjacent to the heart, and an electromagnetic subassembly adapted for mounting on the human body in functionally cooperative relation with respect to the mat. The electromagnetic subassembly includes a plurality of electromagnets. The method includes measuring a pressure at a plurality of location on the electromagnetic subassembly, determining whether the measured pressure at one location on the electromagnetic subassembly is greater than the measured pressure at other locations, and adjusting current being supplied to at least one of the electromagnets if it is determined that the measured pressure at one location on the electromagnetic subassembly is greater than the measured pressure at other locations.

These and other aspects and advantages of the invention will be apparent from the following description, the accompanying drawings, and the appended claims.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
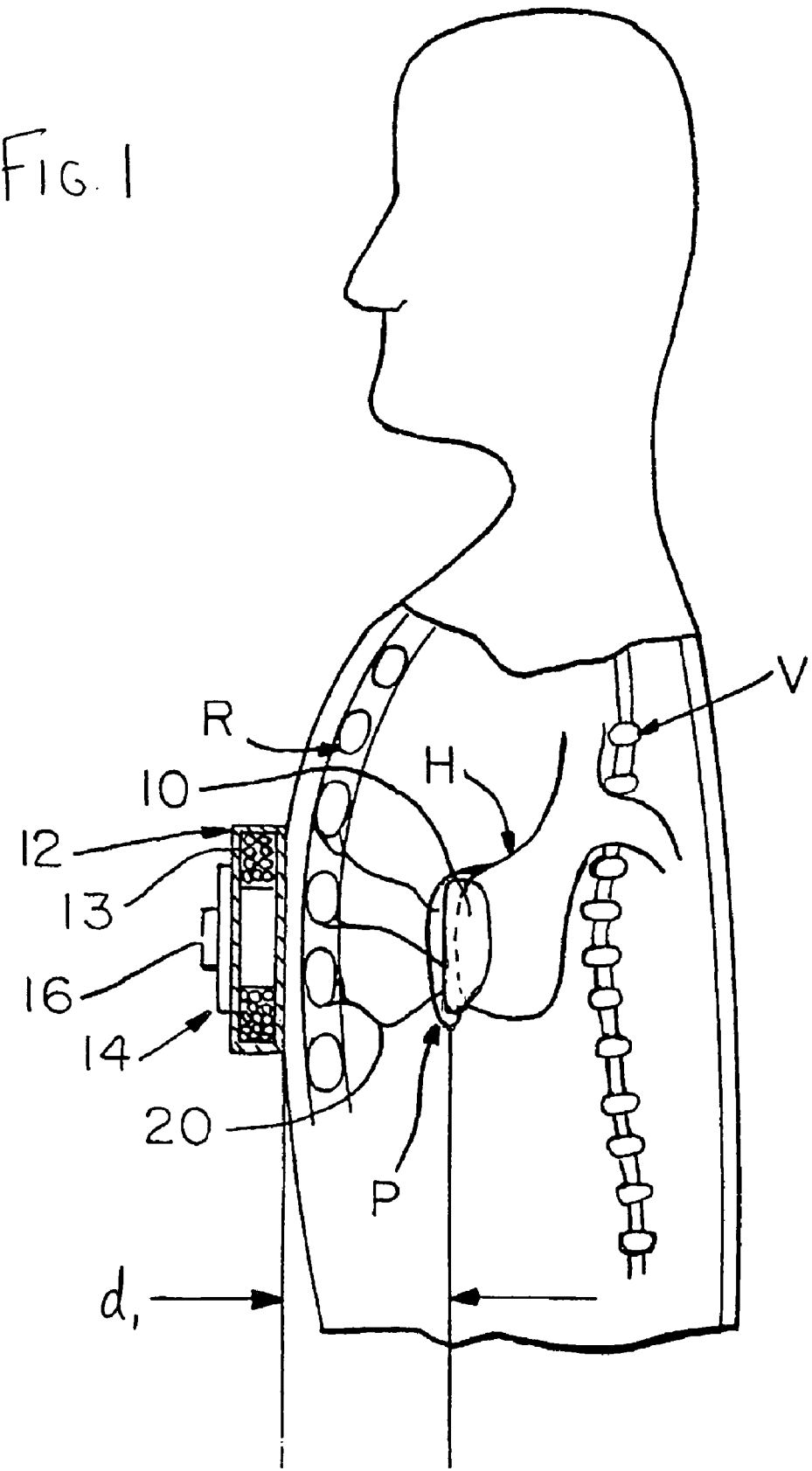
FIG. 1 is a side sectional view of the cardiac assist device, according to an embodiment of the present invention, shown inside the human body in non-compressive relation with the heart.

FIG. 1 is a side sectional view taken through the human body and the cardiac assist device of an embodiment of the present invention, which is shown in non-compressive relation with the human heart.

Figure 2:
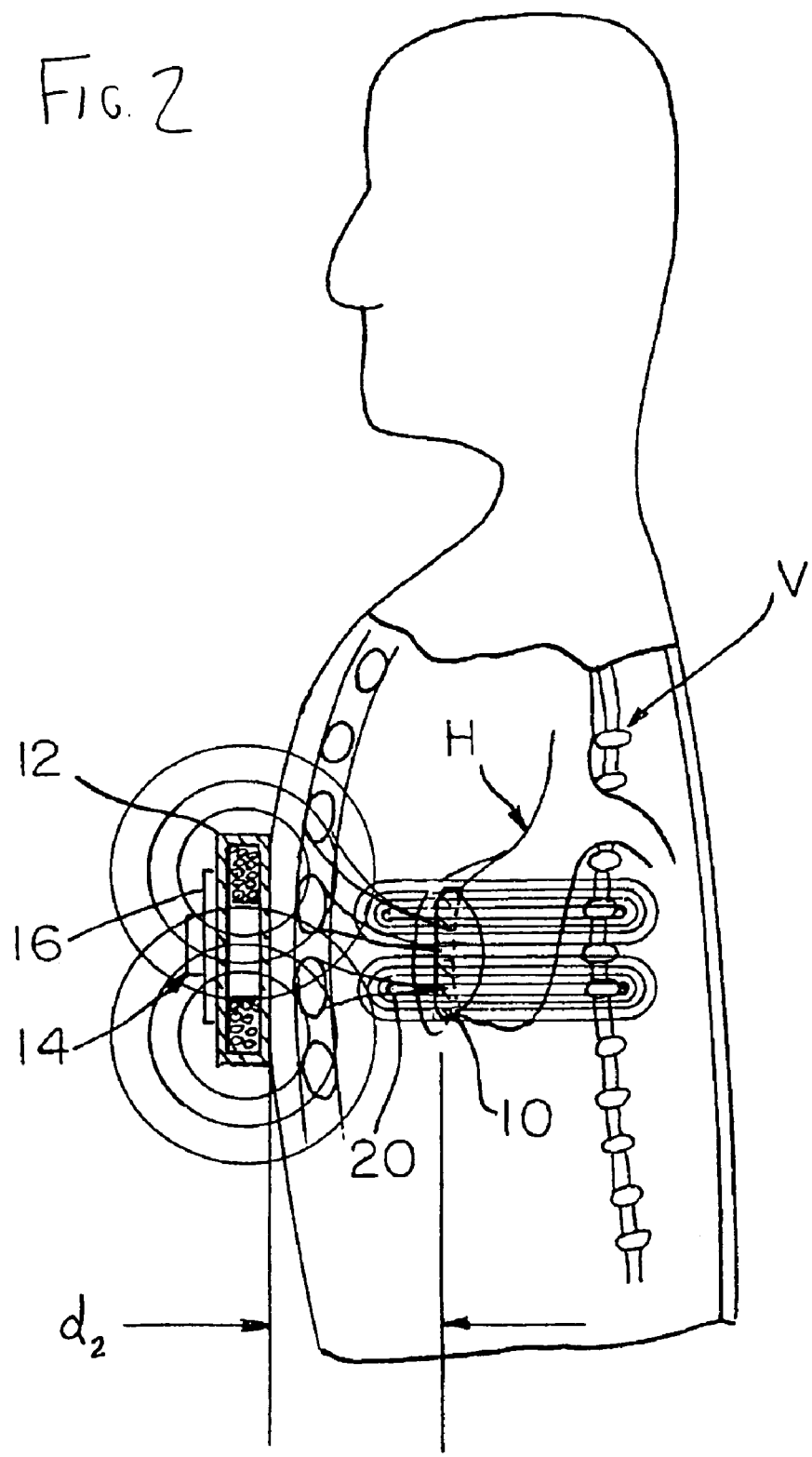
FIG. 2 is a side sectional view of the cardiac assist device of FIG. 1 shown inside the human body in compressive relation with the heart.
Figure 3:
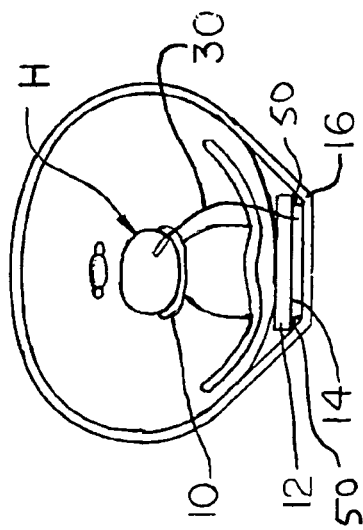
FIG. 3 is a top sectional view showing the cardiac assist device of FIG. 1 inside the human body.

In the illustrated embodiment, the device includes a magnetic mat 10 which is adapted to be mounted inside the human body inside of the rib cage R, adjacent the heart H. Preferably, mat 10 is a permanent magnet made from a ferro-magnetic material, including but not limited to samarium cobalt, neodymium iron, and neodymium iron boron (NeFeBo). It can be appreciated, however, that the mat may comprise other materials (such as a superconductive material) so long as the mat is sufficiently responsive to application of an electromagnetic field to compress the heart in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance including but not limited to polyvinyl chloride (PVC), polytetrafluoroethylene (PTFE), and zinc. As discussed in further detail below, the mat 10 may be custom made for each patient so that the posterior surface of the mat substantially conforms to the anterior surface of the heart, as shown in FIGS. 1-3, without flexing the mat.

In the embodiment illustrated in FIGS. 1-3, the mat is supported within the body, preferably in the space between the anterior aspect of the heart H and the posterior aspect of the pericardium P, although, as will be described later, the mat can also be positioned anteriorly to both the heart and pericardium. Preferably the mat support comprises a plurality of heavy mono-filament threads 20 each having one end secured to the mat and another end secured to the rib cage R (or sternum). The threads are flexible to permit movement of the mat, and should be sufficiently strong to withstand continued flexing without breakage. Where the mat is disposed between the heart and pericardium, the threads 20 are sutured through the pericardium. It can be appreciated that many alternatives to the mono-filament threads can be used to support the mat, as long as such alternatives maintain the mat in movably supported relation, anteriorly and proximate to the heart.

An electromagnetic assembly 12 is adapted to be mounted externally on the human body, preferably on the chest, in functionally cooperative relation with respect to the mat 10, at a distance represented by $d_1$ in FIG. 1. The electromagnetic assembly 12 includes an inductive coil 13 to which a current is supplied (preferably by a D.C. battery, not shown) to produce an electromagnetic field in a first direction, which repels the mat 10 into compressive relation with the heart H, as shown in FIG. 2, which causes the distance between the mat 10 and the electromagnetic assembly 12 to increase to $d_2$. More particularly, electromagnetic assembly 12 alternately generates and discontinues the electromagnetic field to alternately compress the heart against vertebral body V (e.g., the spine) and then permit the heart to relax, thereby assisting the mechanical pumping function of the heart. The magnitude of the force produced will be proportionally dependent on the mat's magnetic field strength, the amount of current traveling through the electromagnetic assembly 12, and the number of current-turns in the electromagnetic assembly 12, but inversely proportional to the distance between the electromagnetic assembly and the mat.

In an embodiment, the electromagnetic assembly 12 may be further arranged to produce an electromagnetic field in a second direction that is opposite the first direction described above. Specifically, the current that is supplied to the coil 13 to generate the electromagnetic field may be reversed, which will cause the electromagnetic field to be reversed, thereby attracting the magnetic mat 10 rather than repelling the mat 10. Further details of such an arrangement are provided in U.S. Provisional Patent Application No. 60/755,416, which is incorporated herein by reference, and U.S. Patent Application Publication No. 2007-0156008 A1, which is incorporated herein by reference.

A transducer 14 (preferably a load cell, force gauge type, made from piezo AC material) is secured to the electromagnetic assembly 12 on the side opposite the chest by a preferably rigid harness 16. The harness is disposed in surrounding relation to the human torso as shown in FIG. 3, which is a top sectional view through the torso. The harness 16 may include shoulder straps to prevent vertical movement of the electromagnetic assembly 12 when an individual is in the upright position.

In an alternative embodiment (not shown), the mat may be positioned anteriorly to both the heart and pericardium. It can be appreciated, however, that it is more preferable to position the mat in the natural space between the heart and pericardium to enable the mat to more effectively compress the heart by being in direct contact therewith. In addition, placement of the mat anteriorly to the pericardium is more difficult since a significant amount of body tissue between the pericardium and sternum must be removed to enable such placement.

Figure 4:
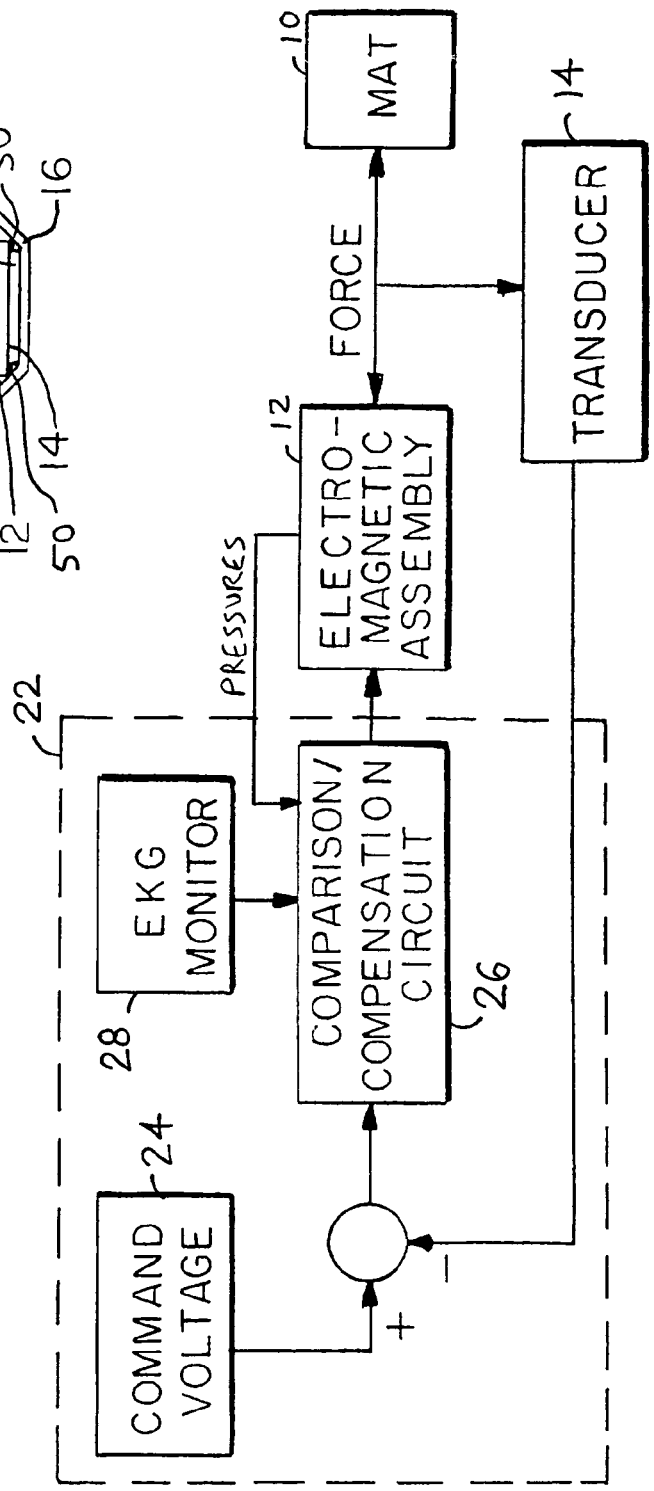
FIG. 4 is a block diagram schematically showing the interrelation of various components of cardiac assist device according to an embodiment of the present invention.

As shown in FIG. 4, the transducer 14 forms part of an electronic feedback/control loop, and functions to evaluate the compressive resistance of the heart during movement of the mat into compressive relation with the heart. More specifically, when the electromagnetic assembly 12 generates an electromagnetic field to repel mat 10, an equal and opposite force is applied to the electromagnetic assembly, thus repelling the assembly away from the chest. It can be appreciated that when such an electromagnetic field is generated, pressure transducer 14 is compressed between the assembly 12 and harness 16 (e.g., see FIG. 2). The transducer 14 senses the compressive pressure or force applied thereto and outputs a voltage proportional to such force or pressure. A control circuit 22 receives the signal generated by the transducer and controls the intensity of said electromagnetic field generated by the electromagnetic assembly as a function of that signal. As a result, the control circuit effectively controls the degree to which the mat compresses the heart.

More specifically, control circuit 22 includes a compensation/comparison circuit 26 (or "compensation circuit") which compares the voltage generated by transducer 14 to a command voltage generated by command voltage generator 24. The command voltage corresponds to a predetermined voltage which represents the ideal amount of force required to compress the heart. The compensation/comparison circuit 26 measures the difference between the voltage generated by the pressure transducer 14 and the command voltage, and then digitally compensates for such difference so that an appropriate amount of current is sent through the coils in the electromagnetic assembly 12. For example, if the voltage generated by transducer 14 is less than the command voltage, the compensation circuit 26 will ramp up the current sent through coils 13 and thereby increase the intensity of the magnetic field applied by electromagnetic assembly 12. In contrast, if the voltage generated by transducer 14 is less than the command voltage, the compensation circuit will decrease the amount of current through coils 13 and thereby decrease the intensity of the magnetic field applied by the electromagnetic assembly 12. Thus, the intensity or magnitude of the electromagnetic field generated by the electromagnetic assembly is controlled so that the compressive force applied by the mat 10 to the heart remains within a predetermined range with each compressive stroke.

The predetermined amount of force to be applied to the heart in order to obtain the desired cardiac output is determined experimentally during an initial procedure wherein a catheter, such as the Swan-Ganz catheter, is placed in the heart to monitor intra-ventricular pressures. This type of catheter is also capable of measuring actual cardiac output. The cardiac output and intra-cardiac pressure are correlated with the voltages generated by pressure transducer 14, and after several days of experimentation, the Swan-Ganz catheter may be removed. The pressure transducer 14 thereafter generates a voltage as a function of the compressive resistance of the heart, which in turn is a function of either the intra-cardiac pressure or output of the heart.

It can be appreciated that the Swan-Ganz catheter may be kept within the heart and utilized as a transducer in lieu of transducer 14. Such an arrangement is shown in FIG. 3, wherein a Swan-Ganz catheter 30 is in place. It is advantageous, however, to remove the Swan-Ganz catheter since use thereof requires the provision of wires extending through the human flesh from the catheter to the electromagnetic assembly 12 and control circuit. This can be quite uncomfortable for the subject.

While the magnitude of the electromagnetic field generated by electromagnetic assembly 12 is controlled by the control circuit 22 together with the pressure transducer 14, it can be appreciated that the frequency of the electromagnetic field must coincide with the natural contractions of the heart. This is accomplished by use of an electrocardiogram (EKG) 28 monitor integrated into the control circuit. The EKG monitor measures the electrical activity of the heart and, together with the rest of the control circuit, functions to synchronize the electromagnetic field generated by the electromagnetic assembly with the QRS spike of the electrocardiogram. This technique of adjusting the rate at which the mat compresses the heart is similar to that used in intra-aortic balloon pumps, and is conventional in this field of technology.

The preferred procedure for inserting the mat 10 into the human body in cooperative relation the heart will now be described. The heavy mono-filament threads 20 each have one end thereof secured to the peripheral edges of two opposite sides of the mat, which preferably has a substantially rectangular or oval shape. An incision is made immediately below the breastbone using the sub-xiphoid approach, and the threads are then sutured to the rib cage and/or sternum by use of curved trochar sheath. The sutures are passed anteriorly to the epicardium, but posterior to the anterior aspect of the pericardium, and exit intercostally lateral to the sternum. Enough slack should be left in the mono-filament sutures to permit movement of the mat 10 away from the electromagnetic assembly 12 into compressive relation with the heart upon application of the electromagnetic field.

In an embodiment of the invention, each patient being considered for cardiac assist with the electromagnetic biventricular assist device described above will first undergo a CAT scan of the chest, preferably with 1.5 mm cuts, to allow a three-dimensional model to be made of that particular patient's heart morphology. The magnetic mat 10 may then be constructed for that unique individual heart morphology. Preferably, the mat 10 is made from neodymium iron boron (NeFeBo) having a zinc coating, although other suitable magnetic materials, such as those described above, may be used. During construction, specific attention is given to the posterior aspect of the magnetic mat so that there is uniform conformity of the posterior surface of the magnetic mat and the anterior surface of the heart. This allows the mat to be constructed so that it substantially conforms to the patient's heart once the mat is inserted into the patient, such as in the manner described above, without having to flex the mat 10. Forming the mat so it substantially conforms with the shape of the patient's heart rather than flexing a flexible mat, as described in the '228 patent, reduces the amount of stress in the mat, which may enhance the stability of the mat.

Figure 5:
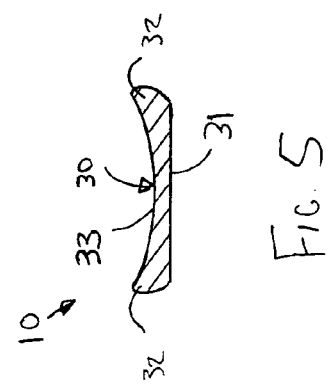
FIG. 5 is a cross-sectional view of an embodiment of a magnetic mat of the cardiac assist device of FIG. 1.

In an embodiment, each magnetic mat is constructed in non-uniform anterior/posterior dimensions. The polarity of the magnetic mat is perpendicular to the relatively flat front surface of the mat, and is set at the time of manufacture of the mat. As shown in FIG. 5, the thickness of the mat is non-uniform, with the thinnest aspect of the mat being at a center portion 30, and the thickest aspect of the mat being at lateral edges 32 of the mat. The anterior surface 31 of the mat 10 should be configured so that it generally falls along the coronal plane of the patient once it is inserted into the patient. The posterior surface 33 of the mat 10 should substantially conform to the anterior morphology of the heart, as specifically delineated from the above-mentioned CAT scan.

Figure 6:
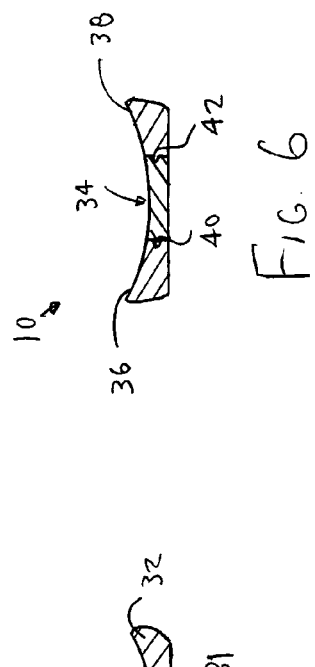
FIG. 6 is a cross-sectional view of another embodiment of the magnetic mat of the cardiac assist device of FIG. 1.

As shown in FIG. 6, the mat may comprise multiple sections. Although three sections are illustrated in FIG. 6, including a center section 34, and lateral edge sections 36 and 38, it is understood that more or less sections may be used. By splitting the mat into sections, the mat may be inserted into the patient in pieces, which may help facilitate the proper positioning of the mat of this embodiment, as the mat of this embodiment does not have a uniform thickness. Although the mat may be constructed initially as a single piece for the uniform fit on the anterior surface of the heart, the single piece may then be divided into somewhat rectangular sections. A tongue-in-groove type hinge 40, 42 may be used to connect adjacent sections to each other, as shown in FIG. 6. Of course, the sections 34, 36, 38 may be connected in other ways. The illustrated embodiment is not intended to be limiting in any way.

By using the mat of the embodiments shown in FIGS. 5 and 6, when the electromagnetic field is generated from the coils 13 in the electromagnetic assembly 12, a greater posterior force will be provided to the lateral edges of the heart, due to the larger amount of magnetic material being at the lateral edges of the mat 10. This allows the pressure to be more evenly distributed across the mat, and the mat will tend to secure itself to the heart, rather than slide off the heart. The shapes of the mats illustrated in FIGS. 5 and 6 provide for a more stable cardiac assist device, because the mat will no longer have a tendency to flip. Of course, other shapes are contemplated as still being within the scope of embodiments of the invention. The illustrated embodiments are not intended to be limiting in any way.

Figure 7:
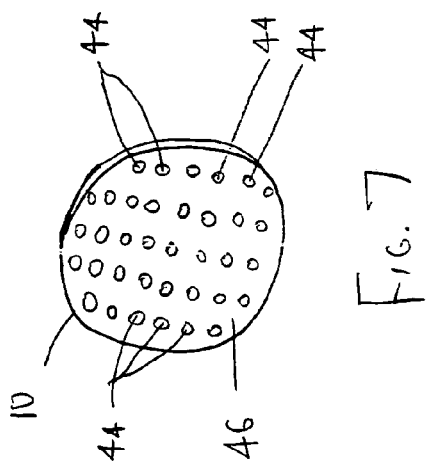
FIG. 7 is a perspective view of another embodiment of the magnetic mat of the cardiac assist device of FIG. 1.
Figure 8:
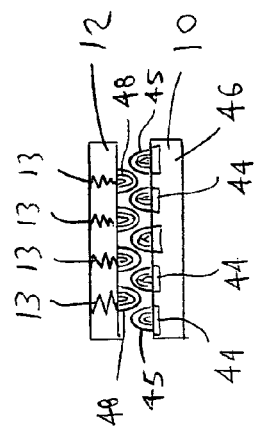
FIG. 8 is a schematic view of electromagnetic fields generated by another embodiment of the cardiac assist device in accordance with the present invention.

In another embodiment, illustrated in FIGS. 7 and 8, the magnetic mat 10 is constructed and arranged to generate a plurality of magnetic fields 45 (see FIG. 8). In the illustrated embodiment, the mat 10 include a series of individual magnets 44 that are arranged in a two-dimensional array and secured to a base mat 46, which is also a solid magnet. The magnetic field generated by this type of magnet morphology will result in a large general magnetic field having the plurality of subfields 45 that create superficial peaks and valleys. In an embodiment, the magnetic mat may actually be manufactured so that the anterior surface of the mat has substantially the same morphology as an egg crate. This "egg crate" morphology provides a different magnetic field than a magnetic field that is generated by a flat disc, which is somewhat rounded and has a polarity that is perpendicular to the flat plane of the disc. The magnetic field generated by the "egg crate" mat may be configured to also have a plurality of magnetic subfields that create peaks and valleys.

As shown in FIG. 8, in order to interface a field that is generated by a magnet that has the morphology of an egg crate, a plurality of electromagnets (e.g., coils 13) may be provided in the electromagnetic assembly 12 in a two-dimensional array. The plurality of coils 13 generates an electromagnetic field different from that generated by a single larger electromagnet. The field generated by the plurality of coils has an irregular surface, due to the generation of a plurality of magnetic subfields 48, which would then interface with the irregular surface of the field generated by the mat 10. This produces an electromagnetic field/magnetic field interface lock, as shown in FIG. 8, which prevents the magnetic mat from being able to flip, yet still allows the cardiac assist device to function properly, as the overall electromagnetic and magnetic fields are still strong enough to create the proper repel force needed to compress the heart.

It is contemplated that the application of the electromagnetic field/magnetic field interface lock that is depicted in FIG. 8 may have broader utility outside of cardiac assist devices, as would be appreciated by those having skill in the art. For example, a relatively simple electromagnetic field/magnetic field interface/capture is disclosed in U.S. Pat. No. 5,182,533 ("the '533 patent"), which is incorporated herein by reference in its entirety. By combining the teachings of the '533 patent with the above-described two-dimensional array, it is contemplated that the field interface lock concept may be used as the basis for a frictionless gear.

When the electromagnetic assembly 12, which includes the array of coils 13, receives current and generates the electromagnetic field that interacts with the magnetic mat 10 located on the heart, there will tend to be an anterior displacement of the electromagnetic assembly 12 relative to the anterior aspect of the chest, as described above. Such a displacement will typically not be uniform; there will be a preference for one corner of the electromagnetic assembly to move anteriorly faster in time and longer in distance more than any other corner of the electromagnetic assembly. The magnetic mat 10 will also tend to move, posteriorly, in the non-uniform fashion relative to the heart, with approximately one quarter of the mat tending to move more posteriorly than any other corner, and one corner tending to move anteriorly.

In an effort to provide uniform posterior displacement of the magnetic mat 10, a non-uniform, real-time electromagnetic field force change may be performed. As illustrated in FIG. 3, piezoelectric sensors 50 may be placed on each corner of the electromagnetic assembly 12 on the anterior aspect of the electromagnetic assembly 12. In a real-time, high frequency fashion, the pressure at each corner is determined. The comparison/compensation circuit, described above, which may be provided on a computer chip in the assembly 12, may be utilized to evaluate the pressure on each corner many times a second. When one corner of the electromagnetic assembly 12 is detected to have more pressure than any other corner, the current to the coils on that corner is reduced in feedback fashion. Simultaneously, the opposite may happen to the opposite corner. Many decisions may be made each second regarding changing the current supplied to the coils on each of the four corners of the assembly 12. This real-time, high frequency pressure sensitive feedback evaluation stabilizes the magnetic mat 10 by providing uniform field interface on each corner/quadrant of the magnetic mat 10, and thus will substantially reduce the tendency of the mat to flip.

While the assembly of the present invention can be used to temporarily assist the mechanical pumping function of the heart (for example, in patients waiting for cardiac transplants, patients with septic shock whose heart is disabled until the endotoxin and/or cardiodepressant factor has been cleared, and patients in cardiogenic shock due to acute ischemia), the invention can also be used as permanent cardiac assist device as it is intended to function for a great number of years with little or no maintenance.

It will be appreciated by one of skill in the art that aspects of the different embodiments of the present invention described above may be combined. It will also be appreciated that the aspects of this invention have been fully and effectively accomplished. It will be realized, however, that the foregoing preferred specific embodiments have been shown and described for the purpose of this invention and is subject to change without departure from such principles. Therefore, this invention includes all modifications encompassed within a spirit and scope of the following claims.

What is claimed is:

1. An electromagnetic cardiac assembly adapted to assist ventricular output in a human heart comprising:
    a magnetic mat adapted for mounting inside a human body adjacent the heart, said mat being made from a material responsive to application of an electromagnetic field so as to be movable in a first direction into compressive relation with the heart in response to application of the electromagnetic field thereto and movable in a second direction out of said compressive relation to permit the heart to relax when application of said electromagnetic field is discontinued, said mat having a shaped, continuous posterior surface that substantially conforms to a shaped anterior surface of the heart for uniform conformity of the shaped posterior surface of the mat and the shaped anterior surface of the heart without flexing said mat when the mat is mounted adjacent the heart; and
    an electromagnetic subassembly adapted for mounting on the human body in functionally cooperative relation with respect to said mat, and for alternately generating and discontinuing said electromagnetic field so that said mat alternately moves into and out of said compressive relation with the heart.

2. The electromagnetic cardiac assembly according to claim 1, wherein the mat comprises at least two sections that are hingedly connected to each other.

3. The electromagnetic cardiac assembly according to claim 2, wherein the mat comprises three sections, and wherein adjacent sections are hingedly connected to each other.

4. The electromagnetic cardiac assembly according to claim 1, wherein the mat has a non-uniform thickness.

5. The electromagnetic cardiac assembly according to claim 4, wherein a center portion of the mat has a thickness that is less than thicknesses of lateral edge portions of the mat.

6. The electromagnetic cardiac assembly according to claim 1, wherein said electromagnetic subassembly is constructed and arranged to reverse said electromagnetic field after said electromagnetic field has been discontinued, and wherein said magnetic mat is responsive to application of the reversed electromagnetic field so as to be movable in the second direction.

7. An electromagnetic cardiac assembly adapted to assist ventricular output in a human heart comprising:
    a magnetic mat adapted for mounting inside a human body adjacent the heart, said mat being made from a material responsive, to application of an electromagnetic field so as to be movable in a first direction into compressive relation with the heart in response to application of the electromagnetic field thereto and movable in a second direction out of said compressive relation to permit the heart to relax when application of said electromagnetic field is discontinued, said mat having a continuous posterior surface and a non-uniform thickness for uniform conformity of the mat and the heart without flexing said mat when the mat is mounted adjacent the heart; and
    an electromagnetic subassembly adapted for mounting on the human body in functionally cooperative relation with respect to said mat, and for alternately generating and discontinuing said electromagnetic field so that said mat alternately moves into and out of said compressive relation with the heart.

8. The electromagnetic cardiac assembly according to claim 7, wherein a center portion of the mat has a thickness that is less than thicknesses of lateral edge portions of the mat.

9. The electromagnetic cardiac assembly according to claim 7, wherein the mat comprises at least two sections that are hingedly connected to each other.

10. The electromagnetic cardiac assembly according to claim 9, wherein the mat comprises three sections, and wherein adjacent sections are hingedly connected to each other.

11. The electromagnetic cardiac assembly according to claim 7, wherein the mat has a posterior surface that substantially conforms to an anterior surface of the heart.

12. The electromagnetic cardiac assembly according to claim 7, wherein said electromagnetic subassembly is constructed and arranged to reverse said electromagnetic field after said electromagnetic field has been discontinued, and wherein said magnetic mat is responsive to application of the reversed electromagnetic field so as to be movable in the second direction.

13. An electromagnetic cardiac assembly adapted to assist ventricular output in a human heart comprising:
    a magnetic mat adapted for mounting inside a human body adjacent the heart, said mat being made from a material responsive to application of an electromagnetic field so as to be movable in a first direction into compressive relation with the heart in response to application of the electromagnetic field thereto and movable in a second direction out of said compressive relation to permit the heart to relax when application of said electromagnetic field is discontinued, said mat being constructed and arranged to generate a plurality of magnetic fields; and
    an electromagnetic subassembly adapted for mounting on the human body in functionally cooperative relation with respect to said mat, and for alternately generating and discontinuing said electromagnetic field so that said mat alternately moves into and out of said compressive relation with the heart, said electromagnetic assembly comprising a plurality of coils constructed and arranged to generate a plurality of electromagnetic subfields that together form said electromagnetic field, said electromagnetic subfields being arranged to extend in between the plurality of magnetic fields created by said mat when said mat and said electromagnetic subassembly are mounted to the human body so as to create a locking relation between said electromagnetic subassembly and said mat.

14. The electromagnetic cardiac assembly according to claim 13, wherein said mat comprises a plurality of magnets that generate the plurality of magnetic fields.

15. The electromagnetic cardiac assembly according to claim 14, wherein the plurality of magnets are arranged in a two-dimensional array.

16. The electromagnetic cardiac assembly according to claim 13, further comprising a controller constructed and arranged to control an amount of current being provided to each of the coils.

17. The electromagnetic cardiac assembly according to claim 16, wherein the electromagnetic subassembly further comprises a plurality of pressure sensors constructed and arranged to measure pressure generated by anterior movement of the electromagnetic subassembly relative to the human body.

18. The electromagnetic cardiac assembly according to claim 17, wherein the controller is configured to receive signals from the plurality of sensors and control the amount of current being provided to each of the coils based on the signals.

19. The electromagnetic cardiac assembly according to claim 17, wherein the pressure sensors are piezoelectric sensors.

20. The electromagnetic cardiac assembly according to claim 13, wherein said electromagnetic subassembly is constructed and arranged to reverse said electromagnetic field after said electromagnetic field has been discontinued, and wherein said magnetic mat is responsive to application of the reversed electromagnetic field so as to be movable in the second direction.

* * * * *